United States Patent
Welker et al.

(10) Patent No.: US 8,202,331 B2
(45) Date of Patent: Jun. 19, 2012

(54) PUMP PURGE APPARATUS AND METHOD

(75) Inventors: Kyle Welker, Sugar Land, TX (US);
Wade L. Williams, Sugar Land, TX (US)

(73) Assignee: Odoreyes Technologies, Inc., Sugar Land, TX (US)

( * ) Notice: Subject to any disclaimer, the term of this patent is extended or adjusted under 35 U.S.C. 154(b) by 926 days.

(21) Appl. No.: 12/245,979

(22) Filed: Oct. 6, 2008

(65) Prior Publication Data

US 2010/0084020 A1    Apr. 8, 2010

(51) Int. Cl.
*C10J 1/28* (2006.01)
*C10J 3/46* (2006.01)
*C01B 3/32* (2006.01)

(52) U.S. Cl. ....... 48/195; 48/127.9; 48/197 R; 48/198.3; 48/127.3; 422/5; 422/123; 422/177; 700/266

(58) Field of Classification Search .................... 48/195; 700/266

See application file for complete search history.

(56) References Cited

U.S. PATENT DOCUMENTS

| | | | |
|---|---|---|---|
| 1,573,106 A * | 2/1926 | Warner | 137/211 |
| 5,406,970 A | 4/1995 | Marshall et al. | |
| 6,142,162 A | 11/2000 | Arnold | |
| 6,208,913 B1 | 3/2001 | Marshall et al. | |
| 6,982,061 B1 * | 1/2006 | Brashear | 422/5 |
| 7,726,358 B2 * | 6/2010 | Hartono et al. | 141/82 |

* cited by examiner

*Primary Examiner* — Kaity V. Handal
(74) *Attorney, Agent, or Firm* — Husch Blackwell LLP

(57) ABSTRACT

When odorant injection systems are inactive, they may accumulate unwanted vapors in the pump mechanism and associated tubing. In order to restart the odorant injection system, it is best to purge the unwanted vapors from the odorant pumps. The present pump purge system facilitates purging of unwanted vapors from odorant injection systems in an environmentally friendly fashion. The pump purge system purifies these vapors before they are vented to atmosphere. In addition, the pump purge system accumulates liquid odorant which is a byproduct of the purging process and stores it in a tank to reduce the likelihood of improper disposal. As an option, the pump purge system may also include a liquid odorant recapture system. The liquid odorant recapture system uses high pressure gas to return accumulated liquid odorant to the odorant injection system to be reused. This liquid odorant recovery system ensures environmentally responsible behavior.

3 Claims, 3 Drawing Sheets

PUMP PURGE APPARATUS AND METHOD

DESCRIPTION OF THE PRIOR ART

Natural gas is a clear, odorless and tasteless gas as it comes from the ground. For safety purposes, odorant is commonly injected into natural gas before it is distributed to customers. There are many prior art odorant injection systems including U.S. Pat. No. 6,142,162 owned by the assignee of the present application, which is incorporated herein by reference. Other odorant injection systems are disclosed in U.S. Pat. Nos. 5,406,970 and 6,208,913 which are owned by Y-Z Industries, Inc. Modern odorant injection systems are often controlled by a programmable logic controller (PLC), a personal computer (PC), a flow computer or some combination thereof. These automatic odorant injection systems often have audit features to confirm and document the odorant injection process.

Those skilled in the art know that unwanted odorant vapors are sometimes vented to atmosphere without any filtration and that liquid odorant is sometimes disposed of using improper techniques. There is a need for an improved apparatus to deal with odorant vapors and to encourage proper disposal and/or reuse of odorant.

SUMMARY OF THE INVENTION

The pump purge apparatus of the present invention is an environmentally friendly way to purify unwanted odorant vapors and encourage proper disposal or reuse of liquid odorant. If an odorant pump has been shut off it tends to accumulate unwanted odorant vapor in the pump mechanism instead of liquid odorant. The odorant pump may not function properly until the pump mechanism is full of liquid odorant. Prior to restarting odorant pumps, it is desirable to bleed off any unwanted odorant vapor from the pump mechanism and refill the pump with liquid odorant.

In the present invention, liquid odorant is stored in a primary odorant storage container or tank, sometimes called an odorant tote, under about 25 psi of nitrogen blanket pressure. The tote may be a large metal container holding 50 gallons or more of liquid odorant. When empty, these totes are returned to the odorant supplier to be refilled. The odorant pumps are used to increase the pressure of the liquid odorant to several hundred psi or even more than a 1000 psi. But before restarting an odorant pump, it should be purged of any unwanted odorant vapor.

To accomplish the purge, a downstream valve on each of the pumps is opened to direct the pump output into a downstream sight glass instead of an odorant injection conduit. To make it easier to see the clear odorant, some visual indicator may be added to the sight glass, such as a plurality of balls or a spinner wheel. When liquid odorant comes into contact with the visual indicator, the operator is given a visual confirmation that the pump mechanism has been refilled with liquid odorant because the sight glass is downstream of the odorant pumps. The valves are then actuated to redirect the pump output to the odorant injection conduit. The odorant injection system may then be restarted to odorize unscented natural gas and/or gasified LNG.

When unwanted odorant vapor is passing through the sight glass with a visual indicator, the unwanted vapor does not turn the spinner wheel. If the visual indicator is a plurality of balls, the balls are stationary when unwanted vapor is passing through the sight glass. The unwanted odorant vapor then flows into the odorant accumulator bleed down tank. The unwanted odorant vapor then flows to a odorant exhaust filter which may be as large as a 55 gallon drum. The odorant exhaust filter is filled with filter media, such as activated charcoal which must be periodically replaced when it becomes contaminated. The odorant exhaust filter reduces the concentration of odorant in the unwanted vapors and the purified vapor is then vented to atmosphere.

Over a period of time, the odorant accumulator bleed down tank may fill up with liquid odorant that accumulates as a result of the purging process. The odorant accumulator bleed down tank could be manually removed and replaced with an empty tank when it becomes full of odorant. In the alternative, the pump purge system could further include a liquid odorant recovery system. The liquid odorant recapture system includes a high pressure gas cylinder connected to the odorant accumulator bleed down tank. Valves and other conduits may be opened to allow high pressure nitrogen or some other inert gas into the odorant accumulator bleed down tank. The nitrogen is at about 2,200 psi. A regulator, not shown, is on the outlet of the high pressure gas cylinder. The outlet pressure of this regulator needs to be set to about 20 psi above the blanket pressure in the liquid odorant tank 12. The pressurized nitrogen forces the liquid odorant out of the odorant accumulator bleed down tank and back into the primary odorant storage container for reuse.

The odorant injection system, pump purge system and/or liquid odorant recapture system may be manually operated. Or in the alternative, the odorant injection system, pump purge system and/or liquid odorant recovery system may be operated by a PLC, a PC, a flow computer or any other electronic means. The odorant injection system, pump purge system and liquid odorant injection system may each have their own stand alone control system or there may be an integrated control system for any combination of these systems.

DETAILED DESCRIPTION OF THE INVENTION

Figure 1:
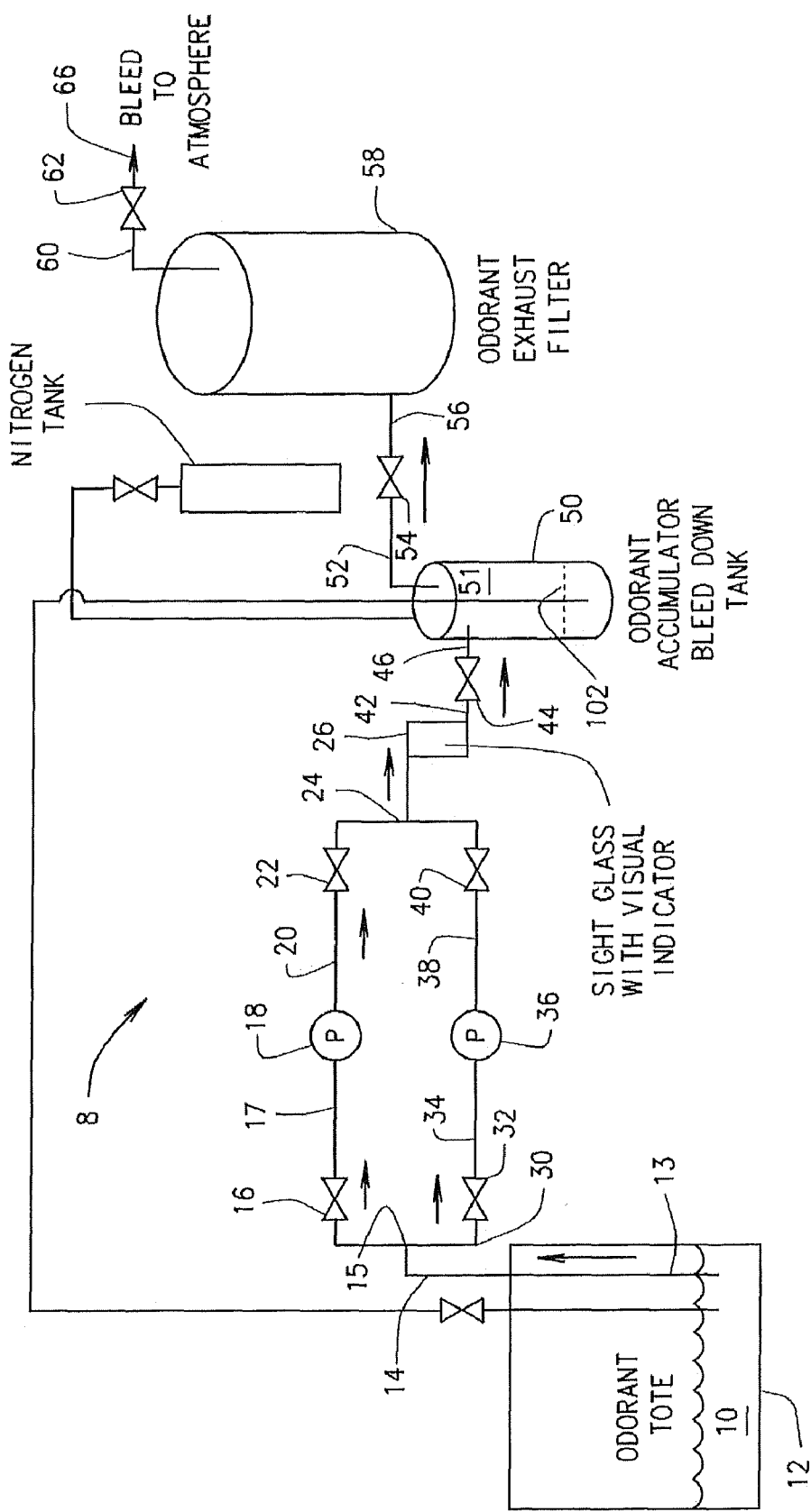
FIG. 1 is a schematic of the pump purge system with flow arrows indicating the flow of odorant and unwanted vapors.

FIG. 1 is a schematic of the environmentally friendly pump purge system 8 with flow arrows indicating the flow of liquid odorant and unwanted vapors. Liquid odorant 10 is held in the primary odorant storage container or tank 12. Odorant flows from the container 12 through a downcomer, 13, a conduit 14, a tee 15, a valve 16, a conduit 17, an odorant pump 18, a conduit 20, a valve 22, a tee 24 to a sight glass 26. As an option, the sight glass may have a visual indicator, such as balls or a spinner wheel. Odorant also flows from the tank through the tee 15, a valve 32, a conduit 34 a second odorant pump 36, a conduit 38, a valve 40, the tee 24 to the sight glass 26.

Unwanted vapors 51 and/or liquid odorant 10 exit the sight glass through the conduit 42 and pass through a valve 44, a conduit 46, and enter the odorant accumulator blow down tank 50. Unwanted odorant vapors 51 exit the odorant accumulator bleed down tank via a conduit 52 and pass through a valve 54, a conduit 56 into the odorant exhaust filter 58. The odorant filter 58 is filled with at least one replaceable filter element, not shown, such as activated charcoal. The at least one filter element is changed periodically when it is contaminated by odorant.

The concentration of odorant in the unwanted vapors 51 is reduced in the odorant exhaust filter and purified vapors 66 exit the filter via a conduit 60 and pass through a valve 62 before being vented to atmosphere via a conduit 64, as indicated by the flow arrow.

Figure 2:
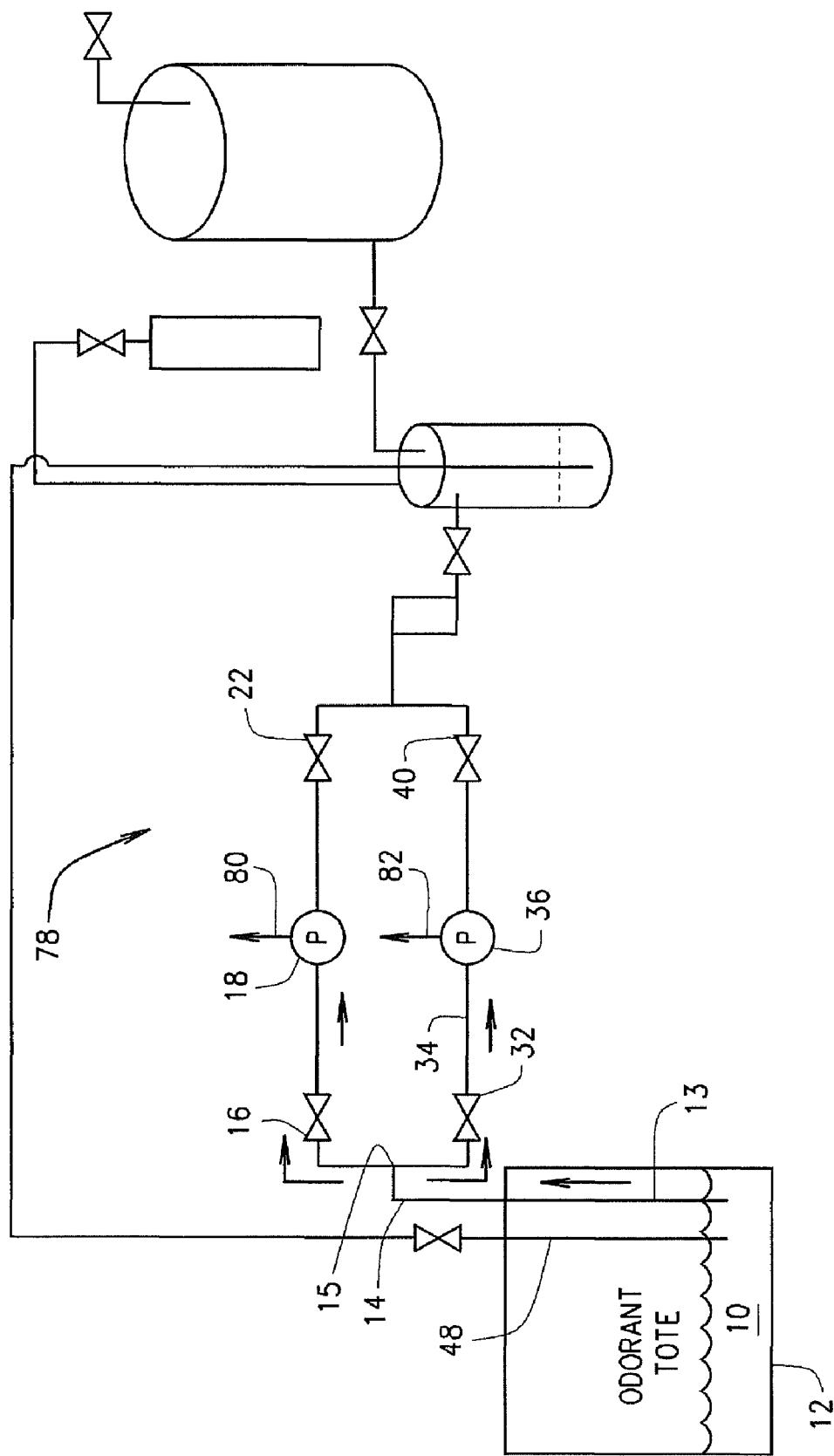
FIG. 2 is a schematic of the odorant injection system injecting liquid odorant into the odorant injection conduits as indicated by the flow arrows.

FIG. 2 is a schematic of the odorant injection system 78 injecting liquid odorant 10 into odorant injection conduits 80 and 82 as indicated by the flow arrows. In this figure, each pump mechanism has been filled with liquid odorant 10 from the tank 12 and valves 22 and 40 have been turned from the on to the off position. As odorant pump 18 continues to operate, liquid odorant flows from the tank 12 as indicated by the flow arrow and exits the pump into the odorant injection conduit 80 to odorize unscented natural gas or gasified LNG. As odorant pump 36 continues to operate, liquid odorant 10 exits the tank, as indicated by the flow arrow, and flows into the odorant injection conduit 82 to odorize unscented natural gas or gasified LNG. Those skilled in the art know that an odorant injection system can have multiple odorant injection conduits as shown in this figure, or both pumps may be injecting into a single odorant injection conduit, not shown.

Figure 3:
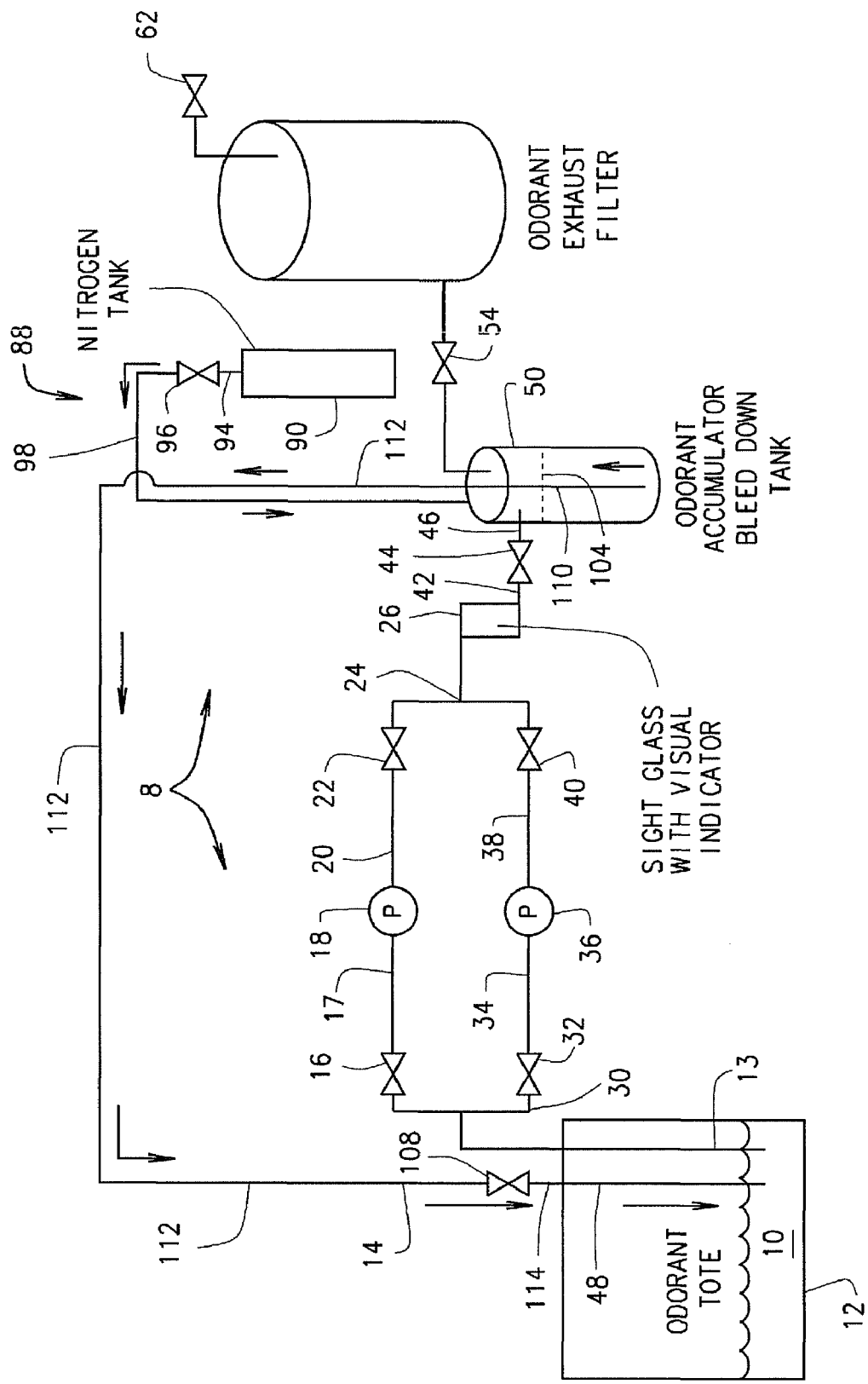
FIG. 3 is a schematic of the liquid odorant recapture system with flow arrows indicating the flow of liquid odorant from the odorant accumulator bleed down tank back into the odorant tank.

FIG. 3 is a schematic of the liquid odorant recapture system 88 with flow arrows in the opposite direction indicating the flow of liquid odorant from the odorant accumulator bleed down tank 50 back into the odorant tank 12. In FIG. 3, the liquid odorant has reached a high level indicated by the line 104 in the odorant accumulator bleed down tank 50 which means tank 50 should be removed and replaced with an empty tank or in the alternative, it needs to be blown down to empty the liquid odorant back into the odorant tank 12 to be reused. In FIG. 1, the liquid odorant was at a relatively low level indicated by the line 102. In FIG. 3, the amount of the liquid odorant has increased in the tank 50 and has risen to the line 104. Over time liquid odorant accumulates in the tank 50 because each purge cycle allows a little liquid odorant to flow through the sight glass. This liquid odorant from each purge cycle accumulates in the tank 50.

In FIG. 3, valves 96 and 108 are in the open position. Valves 44 and 54 are in the closed position. Nitrogen gas 92 is stored in the high pressure nitrogen gas cylinder 90. The pressure in the nitrogen gas cylinder is about 2,200 psi. A regulator, not shown, is connected to the outlet of the gas cylinder. The downstream side of the regulator may be set to about 20 psi above the blanket pressure in the liquid odorant container 12. The nitrogen gas passes from the nitrogen gas cylinder 90, the regulator, not shown, through a conduit 94, the valve 96, a conduit 98 and into the top of the odorant accumulator bleed down tank 50. As the nitrogen gas enters the odorant accumulator bleed down tank 60, the liquid odorant 10, is forced out of the tank 50 into the downcomer 110, the by-pass conduit 112 through the valve 108, the conduit 114 and the downcomer 13 into the primary odorant storage container 12. In this manner, the accumulation of liquid odorant 10 can be substantially reduced in the odorant accumulator bleed down tank 50. The nitrogen gas pressure must exceed the blanket pressure in the primary odorant storage container 12 by about 20 psi in order to force the liquid odorant from tank 50 back into container 12.

Method of Operation

In FIG. 2, an odorant injection system is generally identified by the numeral 78. The odorant injection system may be manually operated or it may have its own control system which may include a PLC, not shown, a PC, not shown, a flow computer, not shown, and combinations thereof. In the alternative, a single control system may operate both the odorant injection system 78, the pump purge system 8 and/or the liquid odorant recapture system 88.

The odorant injection system will typically include at least one primary liquid odorant storage container 12 in fluid communication with at least one odorant pump 18 which is in fluid communication with an odorant injection conduit 80 and a plurality of valves and other conduits. As is well known to those skilled in the art, the liquid odorant is pumped from the primary odorant storage container, through the odorant pump into the odorant injection conduit to add a stinky smell to unscented natural gas or gasified LNG. From time to time, the odorant injection system will be turned off and the odorant pump will temporarily stop operating.

Depending on the amount of time the system is off and other factors, unwanted vapor may accumulate in the pump mechanism and/or the associated conduits. When it is time to restart the odorant injection system, it is best to purge the pump mechanism and associated conduits of the unwanted vapors.

Referring now to FIG. 1, the pump purge system 8 is generally identified by the numeral 8. The pump purge system may be manually operated. In the alternative, the pump purge system 8 may have its own automated control system or be integrated with the odorant injection system 78 and/or the liquid odorant recapture system 88. These control systems may include a PLC, a PC, a flow computer and combinations thereof, not shown.

The purpose of the pump purge system 8 is to remove the unwanted vapors from the odorant injection system 78 and to fill the pump mechanism and associated conduits with liquid odorant, prior to restarting the odorant injection system 78. The pump purge system typically includes at least one sight glass, at least one odorant accumulator bleed down tank, at least one odorant exhaust filter and a plurality of valves and conduits.

When the pump purge system is actuated, the odorant injection lines 80 and 82 are closed, the odorant injection pumps are turned on so the unwanted vapors are captured, purified and vented to atmosphere. The pump purge system works as follows. The valves directing the unwanted vapors to the odorant exhaust filter are opened and the valves to the odorant injection lines 80 and 82 are closed. Then the at least one odorant pump 18 is turned on. The operator then looks at the sight glass 26 to determine when liquid odorant from the odorant tank 12 is passing through the sight glass. Because odorant is a clear liquid, it is helpful, though not required to have some visual indicator in the sight glass to make it easier to tell when liquid odorant is passing through the sight glass. Various types of visual indicators are known to those skilled in the art, including a plurality of balls, a spinner wheel or other apparatus. The unwanted vapors pass through the sight glass into the odorant accumulator bleed down tank 50 and through the odorant exhaust filter 58 which reduces the concentration of odorant in the unwanted vapor before it is vented to atmosphere.

Some liquid odorant may also pass into the odorant accumulator bleed down tank 50 during each cycle of the pump purge system. For example, the line 102 in FIG. 1 indicates a low level of liquid odorant in the tank 50. Over time, the amount of liquid odorant will increase in the tank 50 as indicated by the line 104 in FIG. 3. When the tank 50 has accumulated a sufficient amount of liquid odorant, it may be simply replaced with an empty tank or it may be blown down with nitrogen or some other inert gas.

Referring now to FIG. 3, the liquid odorant recapture system 88 is environmentally responsible because it encourages reuse of liquid odorant instead of disposal, which sometimes leads to inappropriate behavior. The liquid odorant recapture system may use nitrogen gas or any other inert gas that is approved for use in explosive environments. The liquid odorant recapture system 88 includes a high pressure gas cylinder 90 and associated valves and conduits to control the system and direct the flow of the gas to the top of the odorant accumulator bleed down tank 50.

Assuming the tank 50 is about full of liquid odorant as indicated by the line 104, nitrogen gas from the nitrogen cylinder 90 may be fed into the top of the tank 50 as shown by the flow arrows in FIG. 3. This gas forces the liquid odorant through a downcomer 110, a by-pass conduit 112, through a valve 108, through the downcomer 48 and back into the at least one primary odorant storage container 12. This nitrogen recapture system 88 prevents spillage and ensures environmentally responsible behavior.

The invention claimed is:

1. A system for purging unwanted vapors from at least one odorant pump comprising:
    at least one sight glass to determine when the at least one pump is purged of any unwanted vapors;
    an odorant accumulator bleed down tank to receive unwanted vapors and purged fluids from the at least one sight glass with visual indicator;
    an odorant exhaust filter to reduce the concentration of odorant in the vapor when the vapor is periodically vented to atmosphere from the odorant accumulator bleed down tank;
    a plurality of valves to control the pump purge system;
    said at least one sight glass having a visual indicator in the sight glass to make it easier to tell when liquid odorant is passing through the sight glass;
    a nitrogen tank filled with pressurized nitrogen, the nitrogen tank in fluid communication with the odorant accumulator bleed down tank, the pressurized nitrogen periodically forcing accumulated liquid odorant from the odorant accumulator bleed down tank back into a primary odorant storage container;
    means to control the system for purging unwanted vapors from at least one odorant pump; and
    a liquid odorant recapture system.

2. In combination an odorant injection system, a pump purge system, a liquid odorant recovery system, and a control means, the combination comprising:
    the odorant injection system having:
        at least one primary liquid odorant storage container;
        at least one odorant pump; and
        an odorant injection conduit in fluid communication with the at least one odorant pump to inject odorant into unscented natural gas;
    the pump purge system having;
        at least one sight glass in fluid communication with the at least one odorant pump,
        a visual indicator in the sight glass to make it easier to tell when liquid odorant is passing through the sight glass;
        an odorant accumulator bleed down tank to receive unwanted vapors and purged fluids from the at least one sight glass;
        at least one odorant exhaust filter to reduce the concentration of odorant in the vapor when the vapor is periodically vented to atmosphere from the odorant accumulator bleed down tank;
        a plurality of valves to control the odorant injection system and the pump purge system;
    a liquid odorant recovery system including a nitrogen container filled with pressurized nitrogen, the nitrogen container in fluid communication with the odorant accumulator bleed down tank, the pressurized nitrogen periodically forcing accumulated liquid odorant from the odorant accumulator bleed down tank back into the at least one odorant storage container; and
    means to control the odorant injection system for purging unwanted vapors from at least one odorant pump.

3. A method for purging unwanted vapor that has accumulated in at least one odorant pump and recapture of purged liquids, the method including the following steps:
    actuating the at least one odorant pump to displace unwanted vapor from the pump;
    observing a sight glass with visual indicator to determine when liquid odorant has been pumped from at least one odorant container, through the at least one odorant pump and into the sight glass, thus assuring that all unwanted vapor has been displaced from the at least one odorant pump;
    accumulating unwanted vapor and liquid odorant in an odorant accumulator bleed down tank;
    venting, on a periodic basis, the unwanted vapors in the odorant accumulator bleed down tank through an odorant exhaust filter to atmosphere, the odorant exhaust filter reducing the concentration of odorant in the vented vapor; and
    injecting pressurized nitrogen, on a periodic basis, into the odorant accumulator bleed down tank to force any accumulated liquid odorant back into the at least one odorant container.

\* \* \* \* \*